United States Patent
Wofford et al.

(10) Patent No.: US 7,415,095 B2
(45) Date of Patent: Aug. 19, 2008

(54) SYSTEM AND METHOD UTILIZING ADAPTIVE RADIATION THERAPY FRAMEWORK

(75) Inventors: Mark Gregory Wofford, Martinez, CA (US); Ajit Singh, Danville, CA (US); Christopher Amies, Walnut Creek, CA (US); Peter Hoban, Verona, WI (US); Jochen Klaus Kusch, Wachtberg (DE); Stefan Gliessmann, Concord, CA (US); Joerg Stein, Concord, CA (US)

(73) Assignee: Siemens Aktiengesellschaft, Munich (DE)

( * ) Notice: Subject to any disclaimer, the term of this patent is extended or adjusted under 35 U.S.C. 154(b) by 248 days.

(21) Appl. No.: 11/243,056

(22) Filed: Oct. 3, 2005

(65) Prior Publication Data
US 2007/0297565 A1  Dec. 27, 2007

Related U.S. Application Data

(60) Provisional application No. 60/615,269, filed on Oct. 1, 2004.

(51) Int. Cl.
*A61N 5/01* (2006.01)

(52) U.S. Cl. .................................................... 378/65
(58) Field of Classification Search ............... 378/62, 378/65; 382/131, 132; 600/427
See application file for complete search history.

(56) References Cited

U.S. PATENT DOCUMENTS

2004/0254448 A1* 12/2004 Amies et al. ............... 600/410

* cited by examiner

*Primary Examiner*—Courtney Thomas

(57) ABSTRACT

Use of an adaptive radiation therapy framework includes determination of a radiation beam size, radiation beam shape, and radiation beam position for delivering at least a portion of a prescribed radiation dose to a target volume based on first image data of a patient, and selection of one radiation therapy process from an available first process and second process. The first radiation therapy process comprises acquisition of two dimensional image data of the patient, determination of a position offset based on the two-dimensional image data and on the first image data, and movement of the patient based on the position offset. The second radiation therapy process comprises acquisition of three-dimensional image data of the patient, determination of a second position offset based on the three-dimensional image data and on the first image data, and movement of the patient based on the second position offset.

18 Claims, 15 Drawing Sheets

| | IGRT | VGRT | SGRT | DGRT |
|---|---|---|---|---|
| Adaptation | Position | Position | Position | Position |
| Adaptation Process | Rigid 2D Image-to-Image Registration | Rigid 2D Image/Structure-to-Image Registration | Non-Rigid 3D Structure-to-Image Registration | Non-Rigid 3D Dose-to-Image Registration |
| Data Acquired | 2D Images | 3D Image | 3D Image | 3D Image 3D Dose |
| Planning Data | 2D Images | 3D Image Structures | 3D Image Structures | 3D Image Structures 3D Dose |

FIG. 15

SYSTEM AND METHOD UTILIZING ADAPTIVE RADIATION THERAPY FRAMEWORK

CROSS-REFERENCE TO RELATED APPLICATIONS

The present application claims priority to U.S. Provisional Patent Application Ser. No. 60/615,269, filed on Oct. 1, 2004 and entitled "Adaptive Radiation Therapy Unified Framework", the contents of which are incorporated herein by reference for all purposes.

BACKGROUND

1. Field

The embodiments described below relate generally to the delivery of adaptive radiation therapy to a patient. In some embodiments, the degree and/or nature of such adaptivity are selectable and conform to a predefined framework.

2. Description

According to conventional radiation therapy, a beam of radiation is directed toward a tumor located within a patient. The radiation beam delivers a predetermined dose of therapeutic radiation to the tumor according to a treatment plan. The delivered radiation kills cells of the tumor by causing ionizations within the cells.

FIG. 1 illustrates a conventional patient treatment process that includes radiation therapy. According to some examples of process 1, image data of a patient is acquired, and a target volume and critical internal structures are identified based on the image data. A radiation dose is prescribed for achieving desired results with respect to the target volume while minimizing damage to the critical structures. Next, a treatment plan for delivering the dose is determined.

The treatment plan is then delivered to the patient during several sessions, or "fractions", spaced over some period of days. Prior to each fraction, the patient is positioned as required by the treatment plan. Such positioning may involve the use of lasers, skin markers, etc. The relationship between skin markers and the target volume (and other critical structures) is tenuous and may change over time.

However, if relevant portions of the patient are not positioned exactly as required by the treatment plan, the goals of maximizing target radiation and minimizing healthy tissue radiation may not be achieved. More specifically, errors in positioning the patient can result in the delivery of low radiation doses to target tissue and high radiation doses to sensitive healthy tissue. The potential for misdelivery increases with increased positioning errors. Oncologists typically compensate for this potential misdelivery by determining treatment plans that specify lower doses or smaller beam shapes (e.g., beams that do not radiate edges of a tumor) than would be specified if misdelivery was not a consideration.

Systems have attempted to address various aspects of the foregoing. For example, an image of the target volume may be acquired before or after a fraction and reviewed to determine whether the treatment plan is providing the desired results. If not, the patient position or other aspects of the treatment plan may be modified. More efficient adaptation of radiation therapy is desired.

SUMMARY

To address at least the foregoing, some embodiments provide a system, method, apparatus, and means to store first image data of a patient, and select one radiation therapy process from an available first process and second process. The first radiation therapy process includes acquisition of two-dimensional image data of the patient, determination of a position offset based on the two-dimensional image data and on the first image data, and movement of the patient based on the position offset. The second radiation therapy process comprises acquisition of three-dimensional image data of the patient, determination of a second position offset based on the three-dimensional image data and on the first image data, and movement of the patient based on the second position offset.

In some aspects, selection of the one radiation therapy process includes selection of the one radiation therapy process from the first radiation therapy process, the radiation therapy second process, and an available third radiation therapy process. The third radiation therapy process may include acquisition of second three-dimensional image data of the patient, determination of a third position offset based on the second three-dimensional image data and on the first image data, determination of a changed position of at least one internal structure of the patient based on the second three-dimensional image data and on the first image data, movement of the patient based on the third position offset, and determination of at least one of a radiation beam size, a radiation beam shape, or a radiation beam position based on the changed position.

Selection of the one radiation therapy process may include selection of the one radiation therapy process from the first radiation therapy process, the second radiation therapy process, the third radiation therapy process, and an available fourth radiation therapy process. The fourth radiation therapy process includes acquisition of third three-dimensional image data of the patient, determination of a fourth position offset based on the third three-dimensional image data and on the first image data, determination of a second changed position of at least a second one internal structure of the patient based on the third three-dimensional image data and on the first image data, determination of a radiation dose delivered to a target volume of the patient, movement of the patient based on the fourth position offset, determination of at least one of a second radiation beam size, a second radiation beam shape, or a second radiation beam position based on the second changed position, and determination of a second prescribed radiation dose based on the radiation dose and the prescribed radiation dose.

In further aspects, determination of the position offset includes rigid registration of the two-dimensional image data and a digitally-reconstructed radiograph based on the first image data, determination of the second position offset comprises rigid registration of the three-dimensional image data and on fourth three-dimensional image data based on the first image data, determination of the third position offset comprises non-rigid registration of the second three-dimensional image data and on fifth three-dimensional image data based on the first image data, and determination of the at least one of the second radiation beam size, the second radiation beam shape, or the second radiation beam position comprises registration of a portion of the second three-dimensional image data representing the internal structure and the non-rigidly registered fifth three-dimensional image data. Determination of the fourth position offset may include non-rigid registration of the third three-dimensional image data and on sixth three-dimensional image data based on the first image data, determination of the at least one of the third radiation beam size, the third radiation beam shape, or the third radiation beam position may include registration of a portion of the third three-dimensional image data representing the internal structure and the non-rigidly registered sixth three-dimensional image data, and determination of the second prescribed radiation dose may include registration of seventh three-dimensional image data representing the prescribed dose and the non-rigidly registered sixth three-dimensional image data.

Embodiments are not limited to those described herein, as those in the art can readily adapt the descriptions to create other embodiments and applications.

BRIEF DESCRIPTION OF THE DRAWINGS

The construction and usage of embodiments will become readily apparent from consideration of the following specification as illustrated in the accompanying drawings, in which like reference numerals designate like parts, and wherein:

FIG. 15 is a tabular summary of a plurality of adaptive radiation therapy processes according to some embodiments.

DETAILED DESCRIPTION

The following description is provided to enable any person in the art to make and use the embodiments described herein and sets forth the best mode contemplated therefor. Various modifications, however, will remain readily apparent to those in the art.

Figure 1:
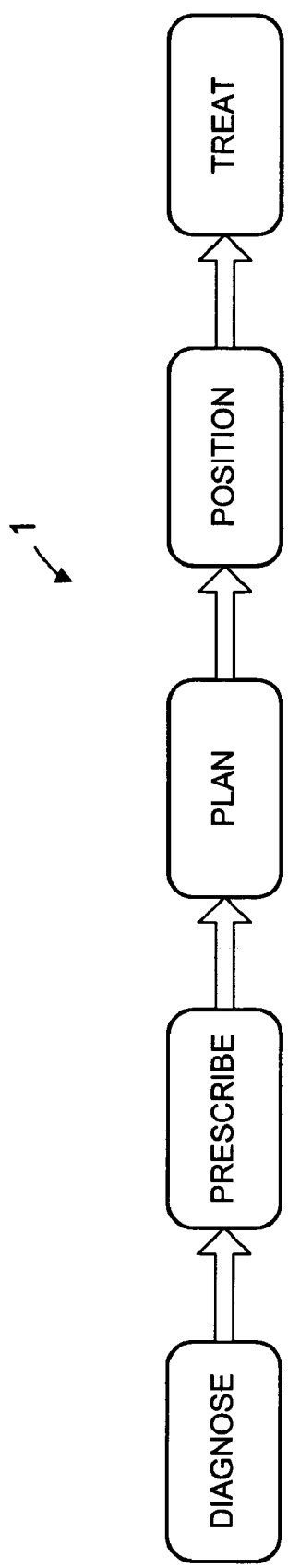
FIG. 1 is a diagram of a conventional radiation therapy process.
Figure 2:
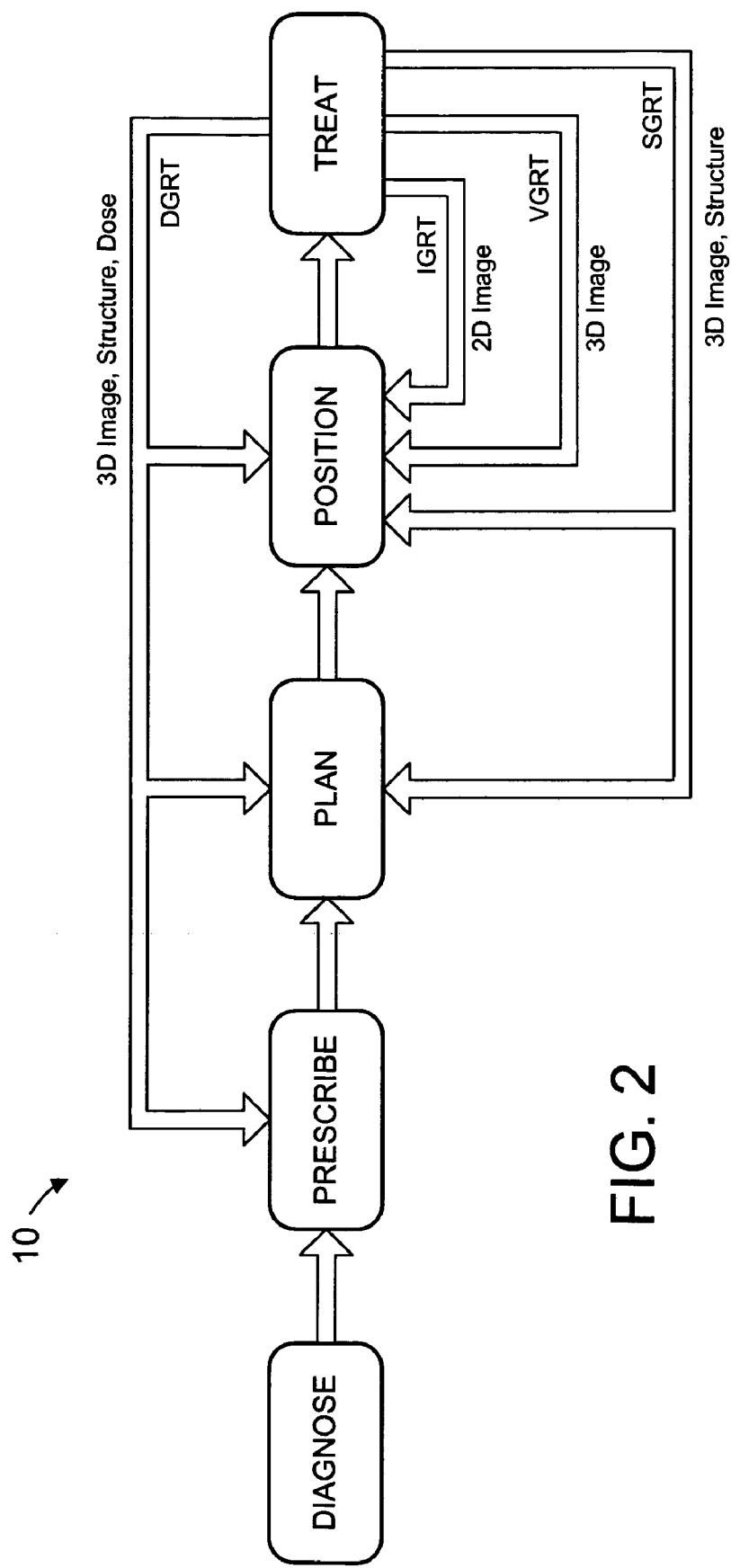
FIG. 2 is a diagram of adaptive radiation therapy processes according to some embodiments.

FIG. 2 is an illustration of several adaptive radiation therapy processes according to some embodiments. Each illustrated process may be implemented by any suitable hardware and/or software elements. Some hardware and/or software elements may be used in the implementation of two or more of the illustrated processes. The illustrated processes are identified by the acronyms IGRT (Image Guided Radiation Therapy), VGRT (Volume Guided Radiation Therapy), SGRT (Structure Guided Radiation Therapy), and DGRT (Dose Guided Radiation Therapy).

Each of the radiation therapy processes may initially involve execution of the illustrated Diagnose, Prescribe, Plan, Position, and Treat steps described in the Background, although the specific implementation of one or more of the steps may differ among two or more of the processes. Unlike the conventional systems described therein, each of the processes includes a "feedback loop" for changing at least one radiation therapy parameter.

The IGRT process, as shown, may determine a change to a patient position (i.e., a patient offset) based on a two-dimensional image acquired before or during the Treat step. The VGRT process, in contrast, may determine a patient offset based on a three-dimensional image acquired before or during the Treat step. More detailed explanations of the IGRT and VGRT processes according to some embodiments are provided below.

The SGRT process involves determination of a patient offset based on a three-dimensional image and on identification of one or more particular structures within a patient. The image and structure(s) may also be used to alter a plan specifying radiation beam parameters. These parameters may include beam shape, beam size, and beam position (i.e., a path traveled by the beam to a target volume).

The DGRT process may include calculation of a received dose over a volume of interest. The calculated dose may be used in conjunction with a three-dimensional image and one or more particular structures within a patient to determine a patient offset, a beam shape, a beam size, a beam position, and a new dose prescription. Treatment may then continue in accordance with the determined patient offset, beam shape, beam size, beam location, and new dose prescription.

According to some embodiments, one or more radiation therapy processes are selectable. The selectable processes may be used to provide desired therapeutic effects as well as efficient use of resources.

Figure 3:
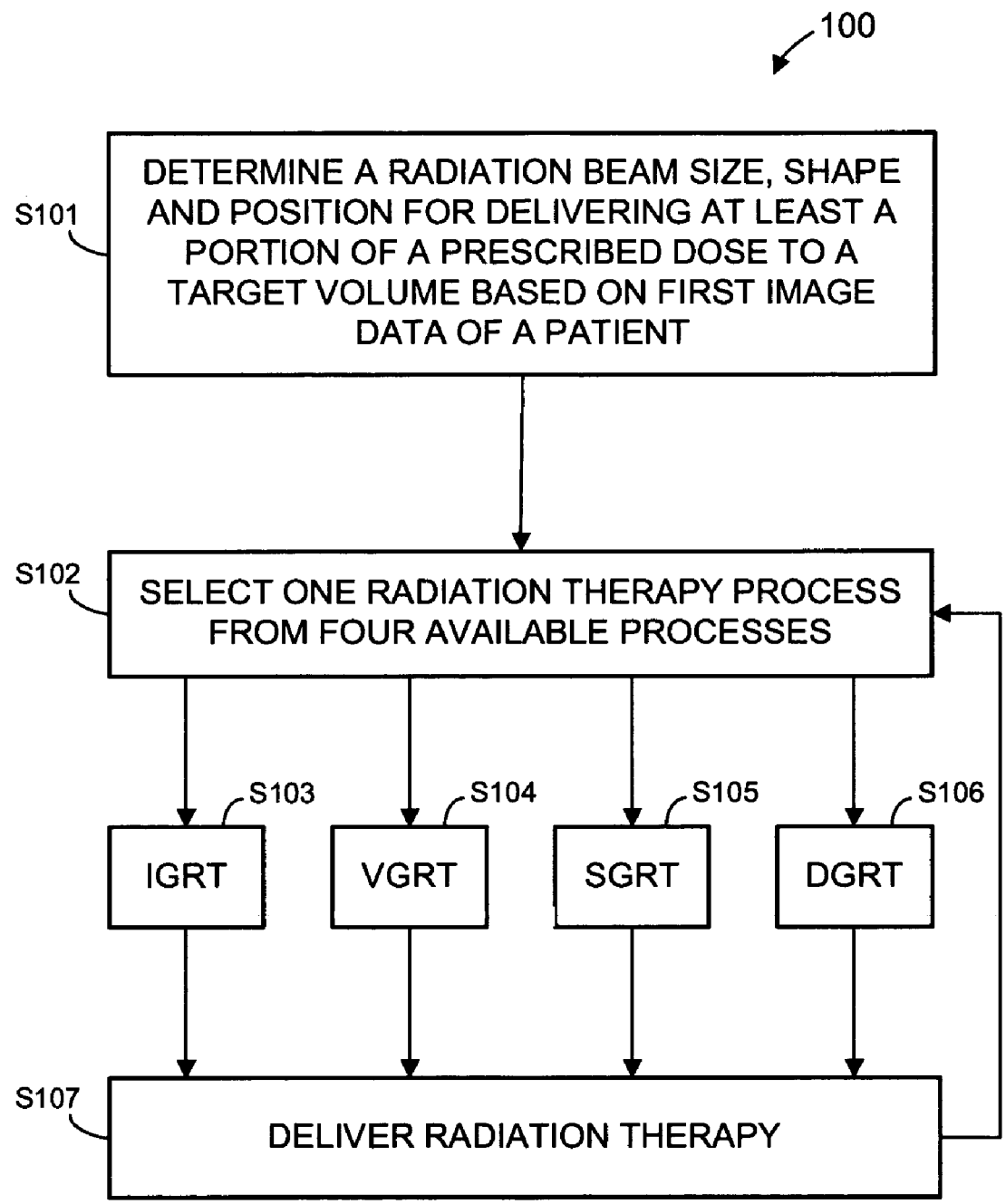
FIG. 3 comprises a flow diagram illustrating process steps according to some embodiments.

FIG. 3 is a flow diagram of process steps 100 according to some embodiments. Process steps 100 may be implemented by any number of hardware and/or software elements, and a portion or all of an illustrated step may be performed manually.

Initially, a radiation beam size, shape and position are determined based on first image data of a patient at S101. The size, shape and position comprise what is referred to herein as a beam plan and are intended to deliver at least a portion of a prescribed dose to a patient. The prescribed dose is specified by a treatment plan determined prior to S101.

Next, at S102, one radiation therapy process is selected from among four available processes. Some embodiments may allow selection from two, three, or more than four available radiation therapy processes at S102. The available processes according to the FIG. 3 embodiment are the aforementioned IGRT, VGRT, SGRT, and DGRT processes. The selection may be performed automatically by a software algorithm or by manual means. In some embodiments, the selection is based on a time since a last fraction was delivered, a margin of error allowed by the treatment plan, a desired accuracy of delivery, an allotted treatment time, and/or any other suitable factors.

The selected process is executed during one of S103, S104, S105 and S106 and flow then proceeds to S107. Radiation therapy is delivered at S107 based on any changes to the treatment plan that resulted from the selected process. Flow then returns to S102 and continues as described above. In some embodiments, process steps 100 terminate after all fractions of the treatment plan have been delivered.

Embodiments of each of the IGRT, VGRT, SGRT, and DGRT processes will be described in detail below. Such embodiments will be generally described in conjunction with system 200, a perspective view of which is provided in FIG. 4. Of course, other systems, some of which are also mentioned below, may be used to implement embodiments described herein.

System 200 includes linear accelerator 210, operator console 220, patient 230, imaging device 240 and table 250. System 200 may be used to generate radiation for imaging and/or for radiation therapy. In this regard, patient 230 is positioned to receive a radiation dose according to a radiation treatment plan.

Linear accelerator 210 may deliver a radiation beam from treatment head 212 toward a volume of patient 230 that is located at an isocenter of accelerator 210. According to some embodiments, the radiation beam may comprise photon or electron radiation having energies in the megavoltage range. Treatment head 212 includes a beam-emitting device (not shown) for emitting a radiation beam and a beam-shielding device, or collimator (not shown) for shaping the beam and for shielding sensitive surfaces from the beam. Treatment head 212 may also include an accessory tray to receive and securely hold attachments used during the course of treatment planning and treatment (such as, for example, reticles, wedges, or the like).

Imaging device 240 may comprise any system to acquire two-dimensional images based on photon radiation (i.e., X-rays) and/or electron radiation received from treatment head 212. Accordingly, imaging device 240 may be suitable for acquiring image data based on megavoltage radiation. Imaging device 240 may be used to acquire images for diagnosis, for verification and recordation of a patient position, for verification and recordation of internal structure positions, and/or for other purposes. Cone-beam reconstruction techniques may be used to construct three-dimensional images from two-dimensional images acquired by imaging device 240.

In some embodiments, imaging device 240 is a flat-panel imaging device using a scintillator layer and solid-state amorphous silicon photodiodes deployed in a two-dimensional array. The RID1640, offered by Perkin-Elmer®, Inc. of Fremont, Calif., is one suitable device. In other embodiments, imaging device 240 converts X-rays to electrical charge without requiring a scintillator layer. In such imaging devices, X-rays are absorbed directly by an array of amorphous selenium photoconductors. The photoconductors convert the X-rays directly to stored electrical charge that comprises an acquired image of a radiation field. Imaging device 240 may also comprise a CCD or tube-based camera. Such an imaging device may include a light-proof housing within which are disposed a scintillator, a mirror, and a camera.

Gantry 214 is rotatable around an axis before, during and after emission of the radiation beam. Rotation of gantry 214 may cause treatment head 210 and imaging device 240 to rotate around the isocenter such that the isocenter remains located between treatment head 210 and imaging device 240 during the rotation.

Imaging device 240 may be attached to gantry 214 in any manner, including via extendible and retractable housing 242. According to the illustrated embodiment, gantry 214 includes compartment 216 into which imaging device 240 and housing 242 may be fully retracted.

Table 250 supports patient 230 during radiation therapy. Table 250 may be adjustable to ensure, along with rotation of gantry 214, that a volume of interest is positioned between treatment head 210 and imaging device 240. Table 250 may be adjusted along any number of axes to account for a determined offset in a position of patient 230.

Operator console 220 includes input device 221 for receiving instructions from an operator and output device 222, which may be a monitor for presenting operational parameters of linear accelerator 210 and/or interfaces for receiving instructions. Such instructions may include a selection from among a plurality of available radiation therapy processes. Output device 222 may also present images acquired by imaging device 240 to verify patient positioning prior to treatment delivery. Input device 221 and output device 222 are coupled to processor 223.

Processor 223 executes program code according to some embodiments. The program code may be executable to control system 200 to operate as described herein. The program code may be stored in storage media of identical or different types, including but not limited to a fixed disk, a floppy disk, a CD-ROM, a DVD-ROM, a Zip™ disk, a magnetic tape, and a signal.

Operator console 220 may be located apart from linear accelerator 210, such as in a different room, in order to protect its operator from radiation. For example, accelerator 210 may be located in a heavily shielded room, such as a concrete vault, which shields the operator from radiation generated by accelerator 210.

Figure 4:
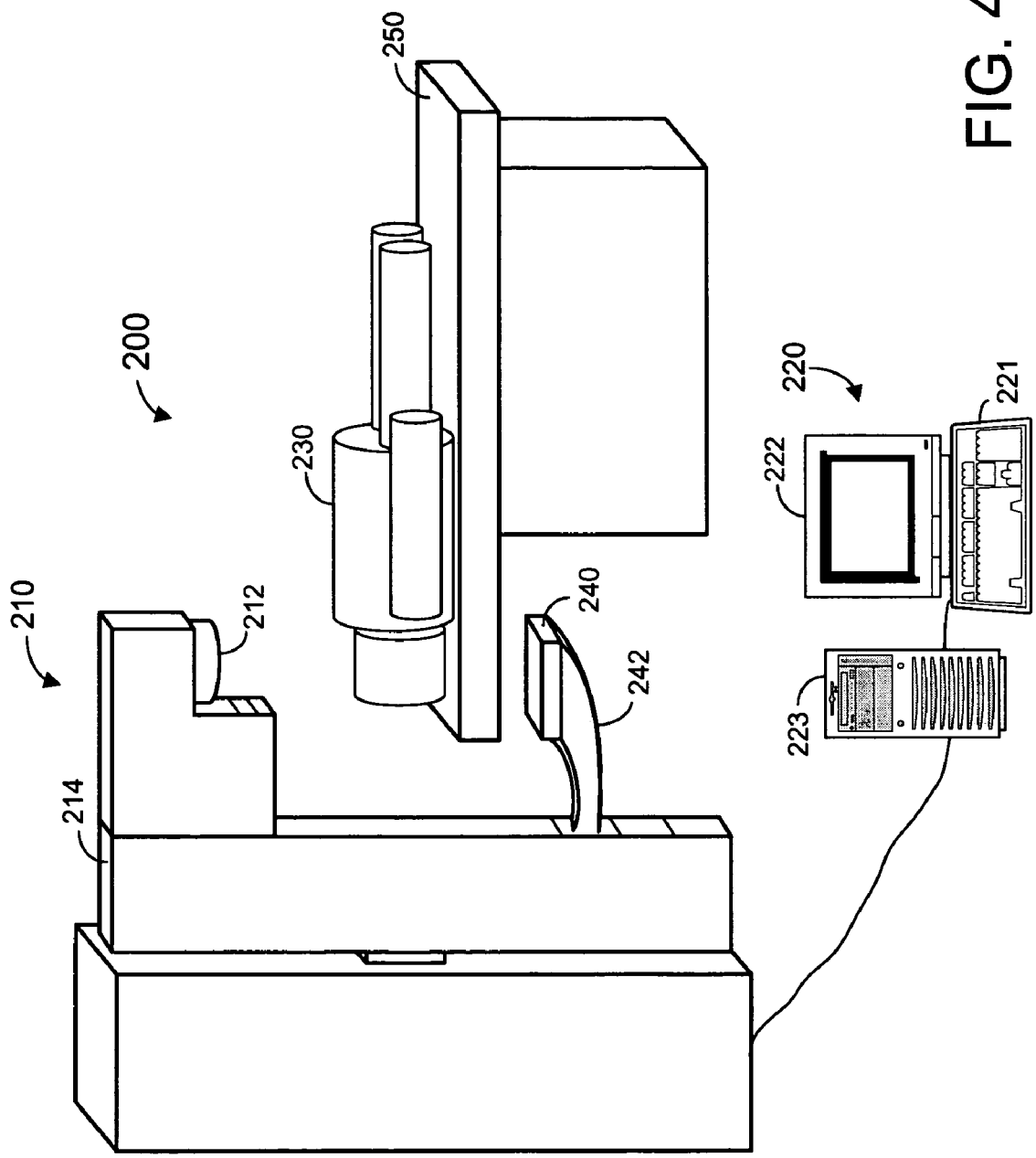
FIG. 4 is a perspective view of a radiation therapy system according to some embodiments.
Figure 5:
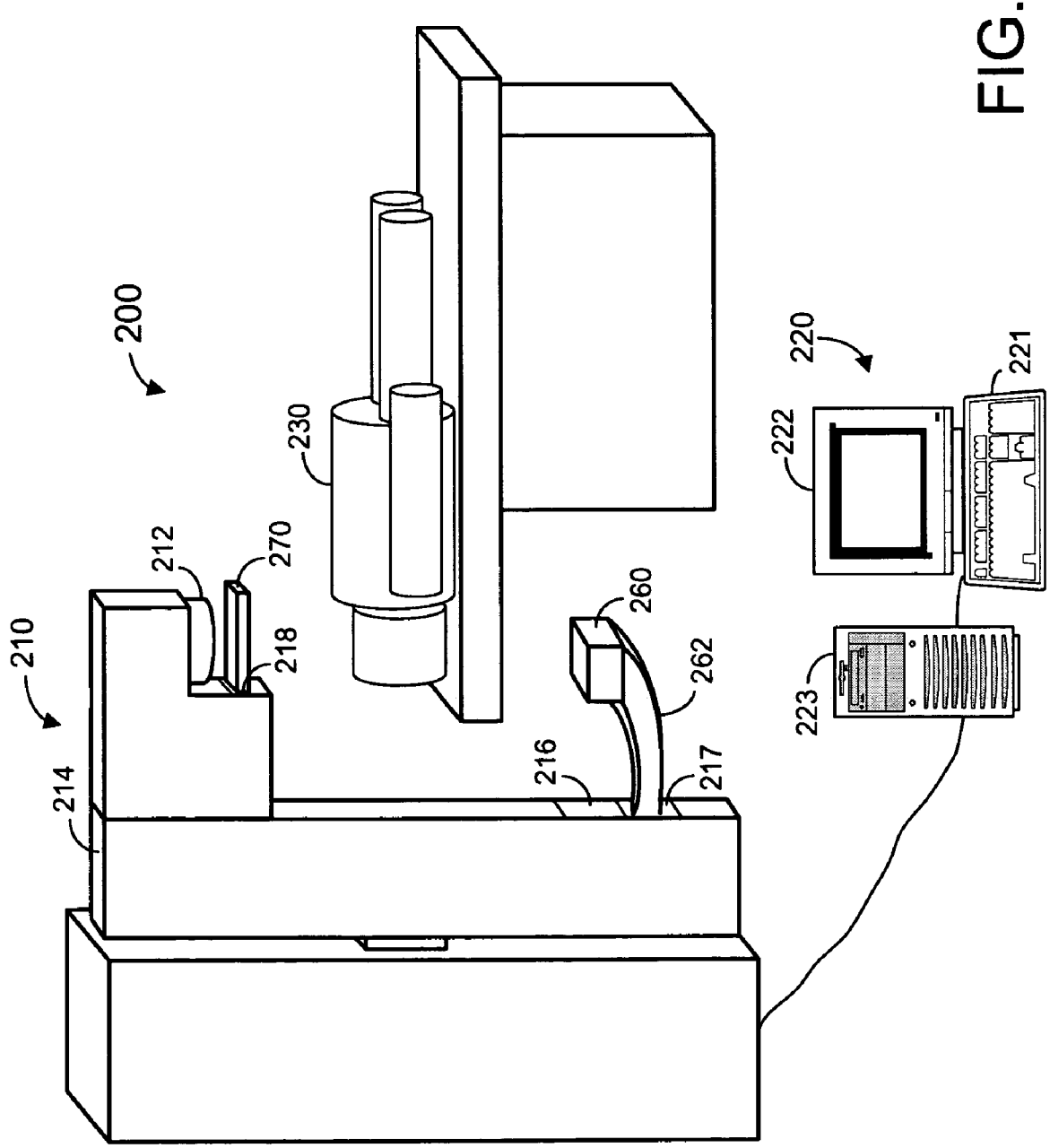
FIG. 5 is a perspective view of a radiation therapy system according to some embodiments.

FIG. 5 illustrates system 200 in a configuration that differs slightly from that illustrated in FIG. 4. As shown, imaging device 240 and housing 242 have been retracted into compartment 216. However, radiation source 260 has been extended from compartment 217 and imaging device 270 has emerged from slot 218 of gantry 214.

Radiation source 260 includes a beam-emitting device such as an X-ray tube for emitting radiation used during calibration, data acquisition and/or treatment. The radiation may comprise electron, photon or any other type of radiation, and may have energies ranging from 50 to 150 keV. Radiation source 260 also may include a concentrator to concentrate the emitted radiation. The concentrator may comprise optics such as a focusing lens for producing a convergent radiation beam from radiation emitted by the X-ray tube. Radiation source 260 may also include beam-shaping devices such as one or more jaws, collimators, reticles and apertures.

Imaging device 270 may comprise any imaging system, including those described above with respect to imaging device 240. Imaging device may acquire two-dimensional images of internal structures of patient. In some embodiments, three-dimensional images are constructed from the two-dimensional images acquired by imaging device 270. Such three-dimensional images may provide better imaging of internal structures of patient 230 than that provided by imaging device 240 in conjunction with treatment head 212.

In some embodiments, linear accelerator 210 comprises the ARTISTE™ linear accelerator sold by Siemens Medical Solutions. Each of the devices shown in FIGS. 4 and 5 may include less or more elements than those shown. In addition, embodiments are not limited to the devices shown in FIGS. 4 and 5.

Figure 6:
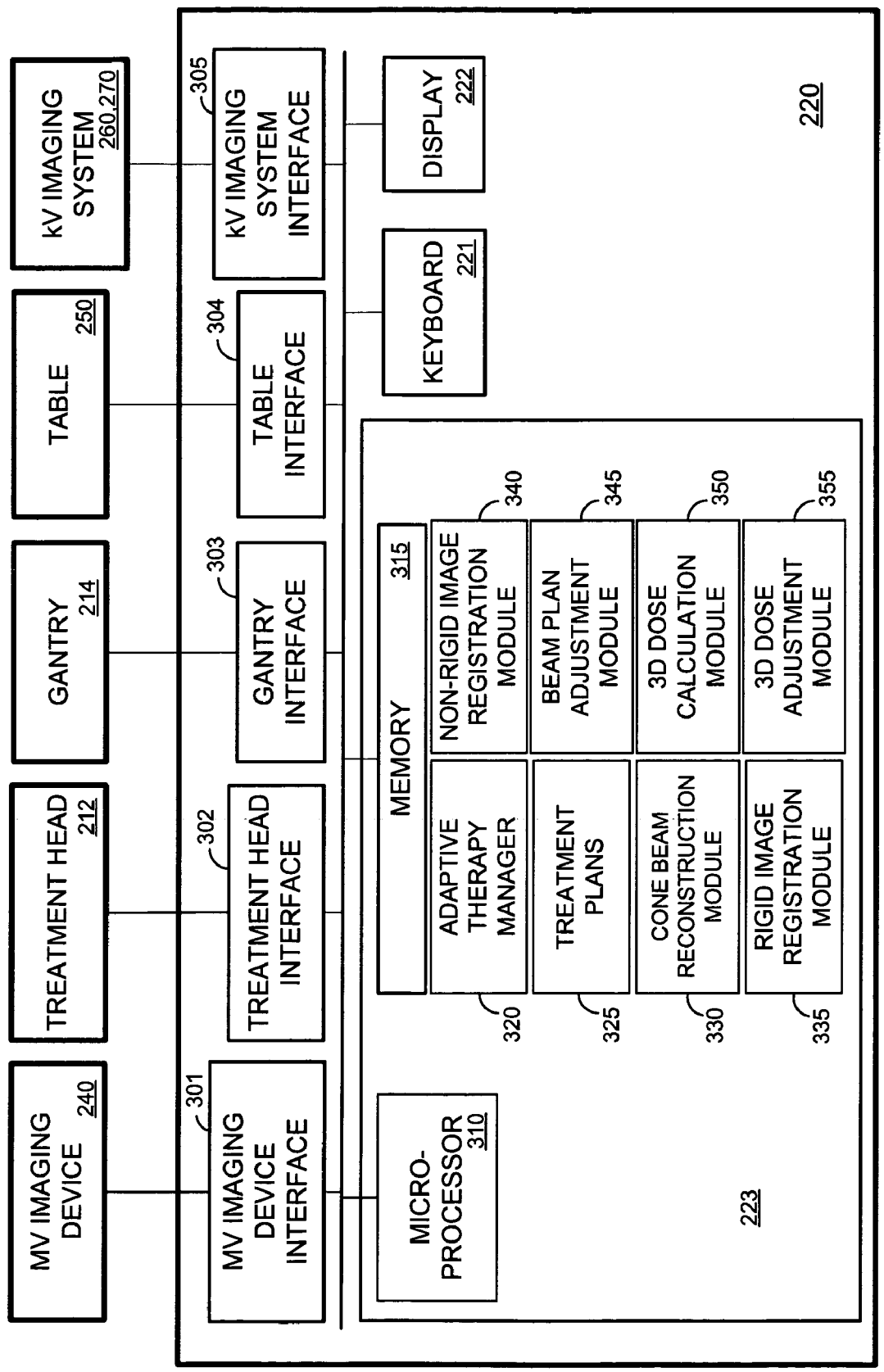
FIG. 6 is a block diagram of a radiation therapy system according to some embodiments.

FIG. 6 is a block diagram of elements of system 200 according to some embodiments. As shown, operator station 220 includes several elements for interfacing with other elements of system 200. Specifically, operator station 220 includes megavoltage imaging device interface 301, treatment head interface 302, gantry interface 303, table interface 304, and kilovoltage imaging system interface 305. Kilovoltage imaging system interface 305, as shown, controls both radiation source 260 and imaging device 270.

Interfaces 301 through 305 may comprise dedicated hardware and/or software interfaces, and one or more of interfaces 301 through 305 may reside in processor 223. One or more of interfaces 301 through 305 may be implemented by a single interface. For example, interfaces 301 and 304 may be implemented by a single Ethernet interface and interfaces 302 through 304 may be implemented by a single proprietary interface for interfacing with table 250, treatment head 212, and gantry 214.

Processor 223 includes microprocessor 310 and memory 315. Microprocessor 310 may execute processor-executable program code stored in memory 315 to provide some or all of the functionality described herein. In this regard, memory 315 stores processor-executable process steps of adaptive therapy manager 320.

Adaptive therapy manager 320 may comprise processor-executable program code to implement process steps 100. Adaptive therapy manager 320 may also comprise program code to generate and/or modify a treatment plan according to some embodiments. In this regard, adaptive therapy manager 320 may comprise the KONRAD™ treatment planning system sold by Siemens Medical Solutions.

Memory 315 may also store treatment plans 325 in accordance with any currently- or hereafter-known format. Treatment plans 325 may comprise scripts that are automatically executable by linear accelerator 210 and treatment table 250 to provide radiation therapy fractions. Treatment plans 325 may include one or more treatment plans in which a patient position, a beam plan, and/or a prescribed dose have been changed according to some embodiments.

Memory 315 also stores cone beam reconstruction module 330, rigid image registration module 335, non-rigid image registration module 340, beam plan adjustment module 345, three-dimensional dose calculation module 350, and three-dimensional dose adjustment module 355. Usage of each of modules 330 through 355 will be discussed below, and may comprise any suitable program code to perform the functions attributed thereto. Modules 330 through 355 may comprise any suitable software format, including but not limited to a dynamic link library, a plug-in, an operating system extension, a standalone application, etc. Adaptive therapy manager 320 may comprise any or all of modules 330 through 355 according to some embodiments.

Figure 7:
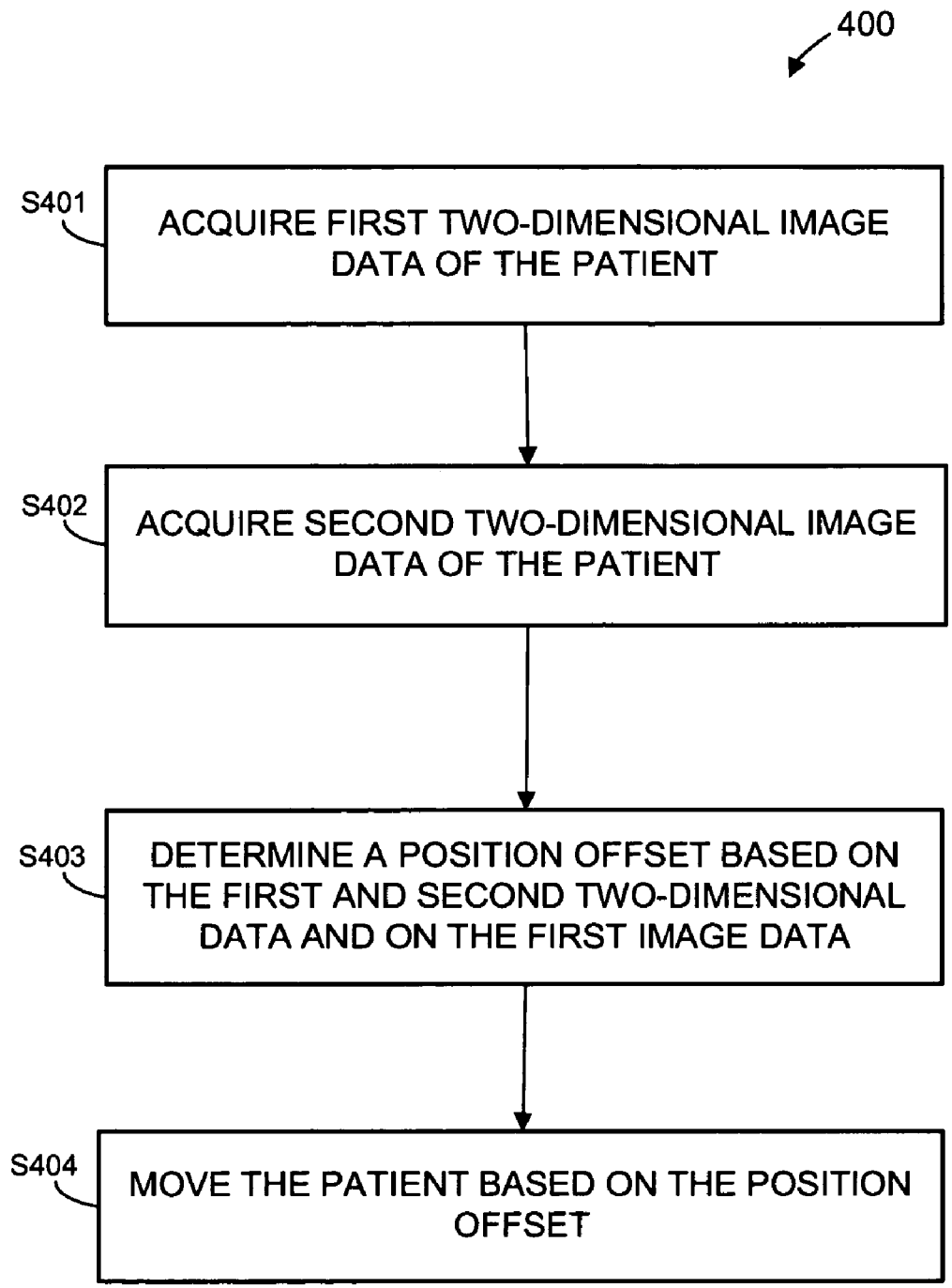
FIG. 7 comprises a flow diagram illustrating an adaptive radiation therapy process according to some embodiments.

FIG. 7 is a flow diagram of step S103 of process steps 100. More specifically, process steps 400 are intended to represent an IGRT process according to some embodiments. Process steps 400, as well as all other process steps described herein, may be embodied in whole or in part by hardware of and/or software executed by elements including but not limited to those of system 200. Software (i.e., program code) embodying one or more of the process steps may be stored by any medium, including a fixed disk, a floppy disk, a CD-ROM, a DVD-ROM, a Zip™ disk, a magnetic tape, or a signal. Some or all of such software may also be stored in one or more devices.

Process steps 400 will be described in the context of process steps 100. The description will therefore assume that, prior to process steps 400, step S101 has been executed and that the IGRT process was selected at step S102.

First two-dimensional image data of the patient is acquired at S401. FIG. 5 illustrates S401 according to some embodiments. Operator station 220 may control radiation source 260 to emit radiation and imaging device 270 to acquire an image based on the emitted radiation. The image comprises a set of data that represents the attenuative properties of tissues that lie between radiation source 260 and imaging device 270. The image may be referred to as a projection image.

Figure 8:
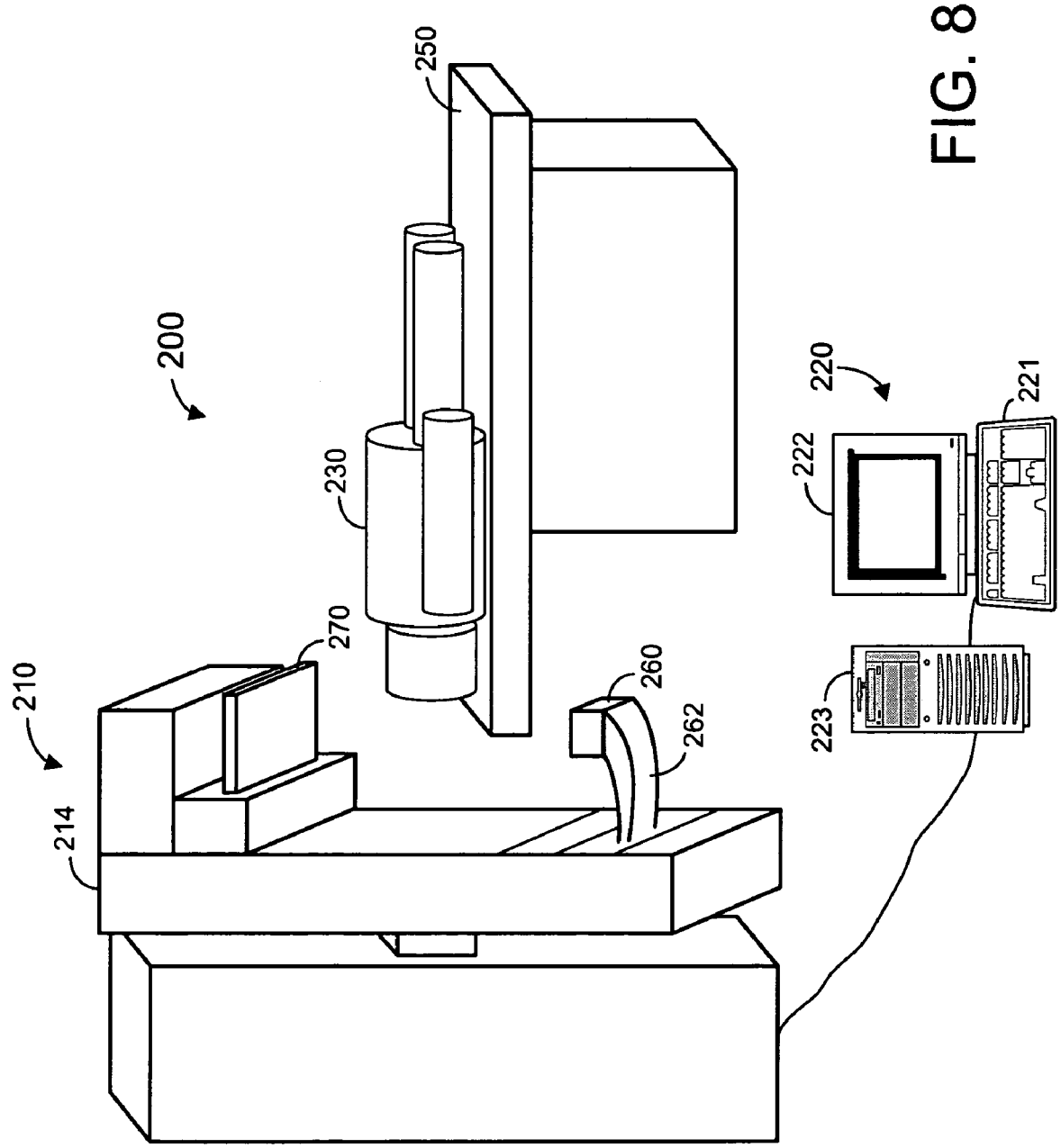
FIG. 8 is a perspective view of a radiation therapy system according to some embodiments.

Second two-dimensional image data is acquired at S402. The second two-dimensional data may be acquired from a projection angle different from that used to acquire the first two-dimensional data. Continuing with the above example, FIG. 8 illustrates rotation of gantry 214 to acquire the second two-dimensional data. Although gantry 214 has rotated from the position shown in FIG. 7, a same internal portion of patient 230 remains between radiation source 260 and imaging device 270 at both projection angles. Again, radiation source 260 is controlled to emit radiation and imaging device 270 is controlled to acquire an image of patient 230 based on the emitted radiation.

Next, a position offset is determined at S403 based on the first and second two-dimensional data and on the first image data that was described with respect to process steps 100. The position offset may comprise a set of data indicating a direction and distance that patient 230 should be moved to comply with a patient position required by the treatment plan. For example, the position offset may comprise a distance along the X-axis, a distance along the Y-axis, and a distance along the Z-axis.

As mentioned above, the first image data used in step S403 comprises data used to determine a beam shape, size, and position. The first image data may comprise two-dimensional or three-dimensional data.

Operator station 220 may determine the position offset by executing program code of rigid image registration module 335 to perform a two-dimensional rigid image-image registration based on the first image data and the acquired first two-dimensional image data and/or the acquired second two-dimensional image data. The rigid image registration may comprise any suitable steps that are or become known.

In some embodiments, the first image data comprises two digitally-reconstructed radiographs representing the projection angles at which the first two-dimensional image data and the second two-dimensional image data were acquired. Accordingly, the determination of the position offset comprises rigid image registration of the acquired first two-dimensional image data with a corresponding one of the two radiographs and rigid image registration of the acquired second two-dimensional image data with the other radiograph.

The patient is moved at S404 based on the determined position offset. Such movement is intended to move the patient into a position required by the treatment plan to be delivered. According to some embodiments, operator station 220 controls table 250 to move the patient based on the determined position offset. For example, if the position offset indicates that the patient is 2 cm too far from treatment head 212 and 3 cm too close to gantry 214, table 250 may be controlled to raise 2 cm and move 3 cm away from gantry 214.

Figure 9:
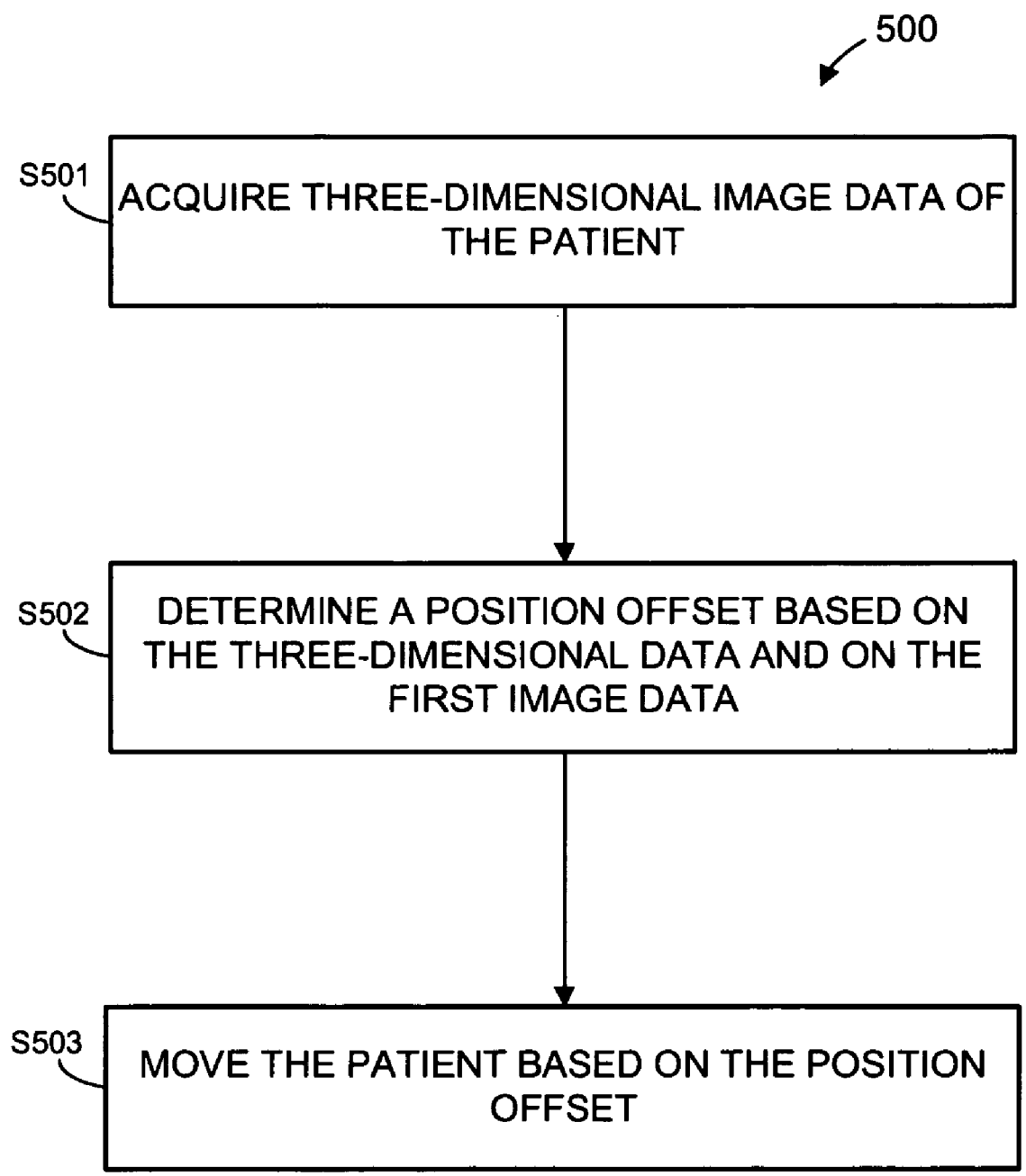
FIG. 9 comprises a flow diagram illustrating an adaptive radiation therapy process according to some embodiments.

FIG. 9 is a flow diagram of step S104 of process steps 100. Process steps 500 therefore represent a VGRT process according to some embodiments. Again, the description of process steps 500 will assume that step S101 has been executed and that the VGRT process was selected at step S102.

Three-dimensional image data of the patient is acquired at S501. Step S501 may comprise acquiring first and second three-dimensional image data with radiation source 260 and imaging device 270 as described with respect to process steps 400, and executing cone beam reconstruction module 330 to generate the three-dimensional image data from the acquired two-dimensional images. Any suitable cone beam reconstruction technique may be used, and may use additional two-dimensional images acquired from additional projection angles.

Figure 10:
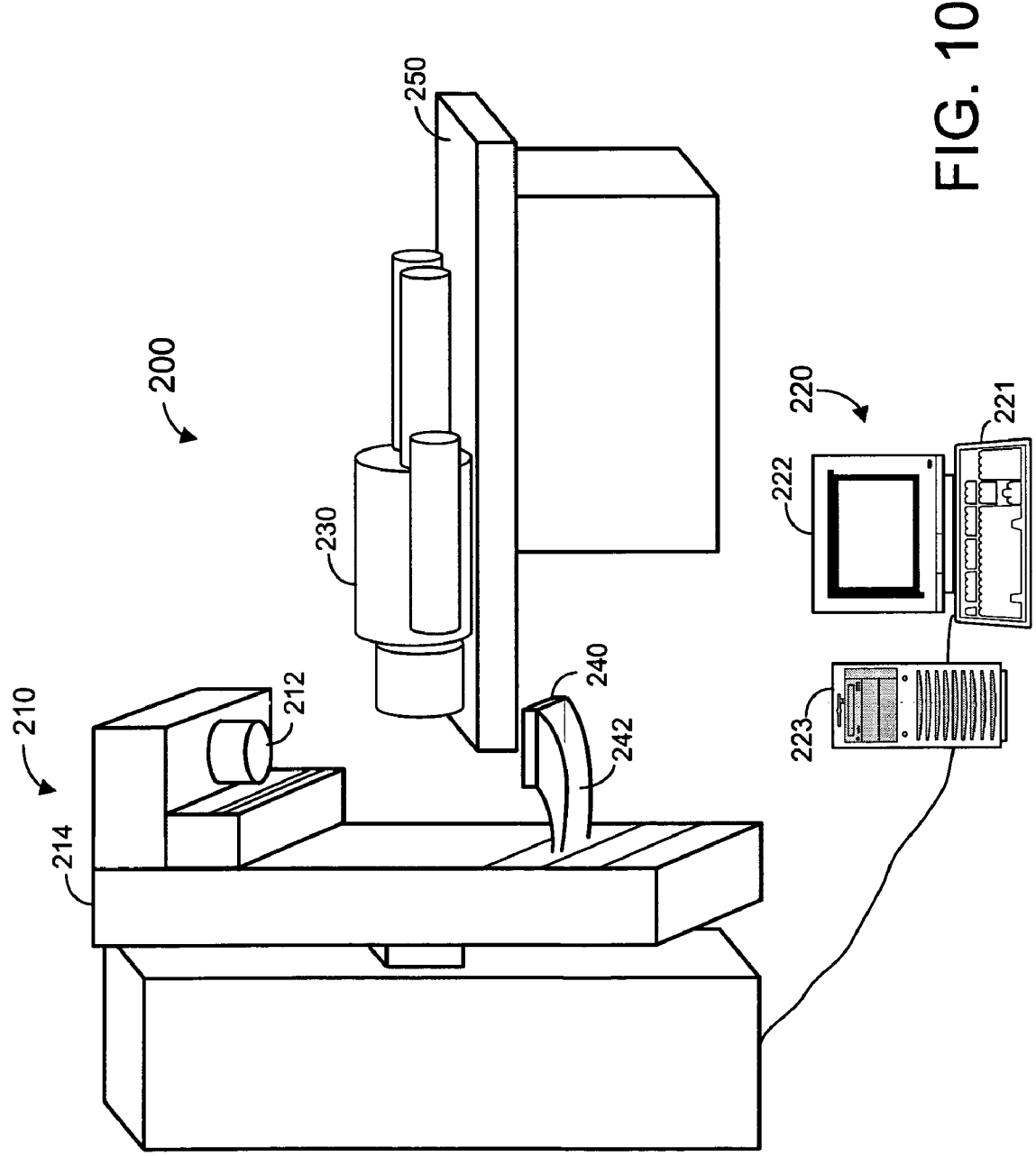
FIG. 10 is a perspective view of a radiation therapy system according to some embodiments.

FIG. 10 illustrates S501 according to some embodiments. As shown, the three-dimensional image data is acquired using treatment head 212 and imaging device 240. Such a scenario may be referred to as megavoltage imaging, and may require treatment head 212 and imaging device 240 to employ different beam and image acquisition, respectively, that those used for during treatment.

According to FIG. 10, patient 230 remains positioned on table 250 while treatment head 212 and imaging device 240 are rotated around a portion of patient 230. At various points during the rotation, operator station 220 may control radiation source 260 to emit imaging radiation and imaging device 240 to acquire a projection image based on the imaging radiation. Processor 223 may then execute program code of cone beam reconstruction module 330 to create three-dimensional image data of the portion of patient 230 based on the acquired projection images.

Figure 11A:
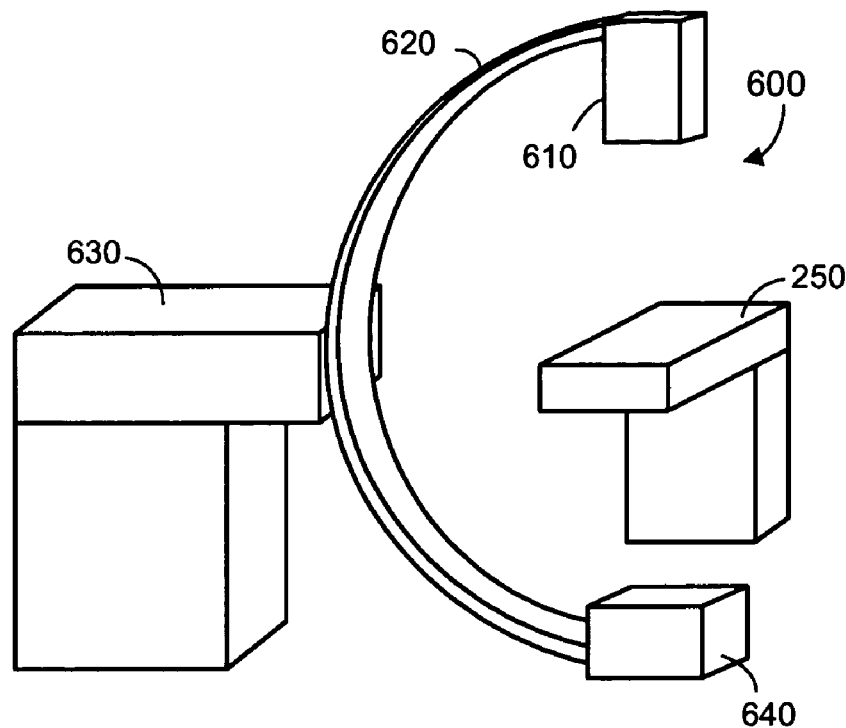
FIGS. 11A and 11B are perspective views of an imaging system according to some embodiments.
Figure 11B:
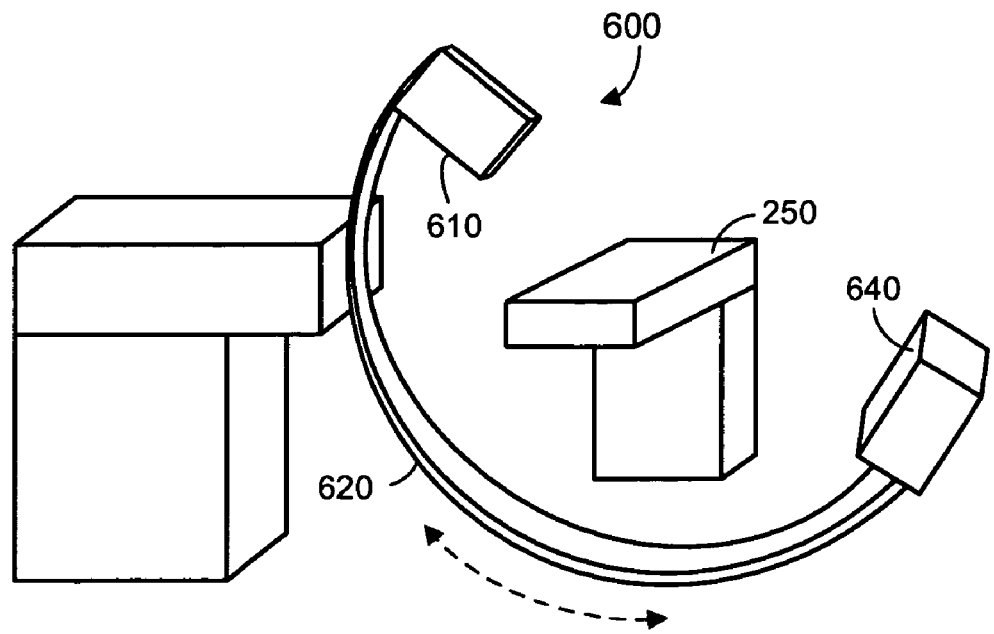

FIGS. 11A and 11B illustrate a system to acquire the three-dimensional image data according to other embodiments.

Mobile cone beam kilovoltage scanner 600 may be moved into the illustrated position with respect to table 250 prior to step S501. Scanner 600 includes X-ray tube 610, C-arm 620, base 630 and imaging device 640.

Scanner 600 may be operated by operator station 220 and/or another device to acquire two-dimensional projection images of patient 230 at the projection angles shown in FIGS. 11A and 11B. Projection images may be acquired at other projection angles as well. More specifically, C-arm 620 may move orbitally around a portion of patient 230 such that the portion remains between tube 610 and imaging device 640. According to some embodiments, C-arm 620 may move in either direction indicated by the dashed line of FIG. 11B to acquire projection images of the portion at various projection angles. The acquired projection images may be used to generate the three-dimensional image data as described above. According to some embodiments, scanner 600 may comprise one of the SIREMOBIL™, ARCADIS™, BICOR™ and AXIOM™ systems sold by Siemens Medical Solutions or other systems designed to perform tomography and/or angiography.

Figure 12:
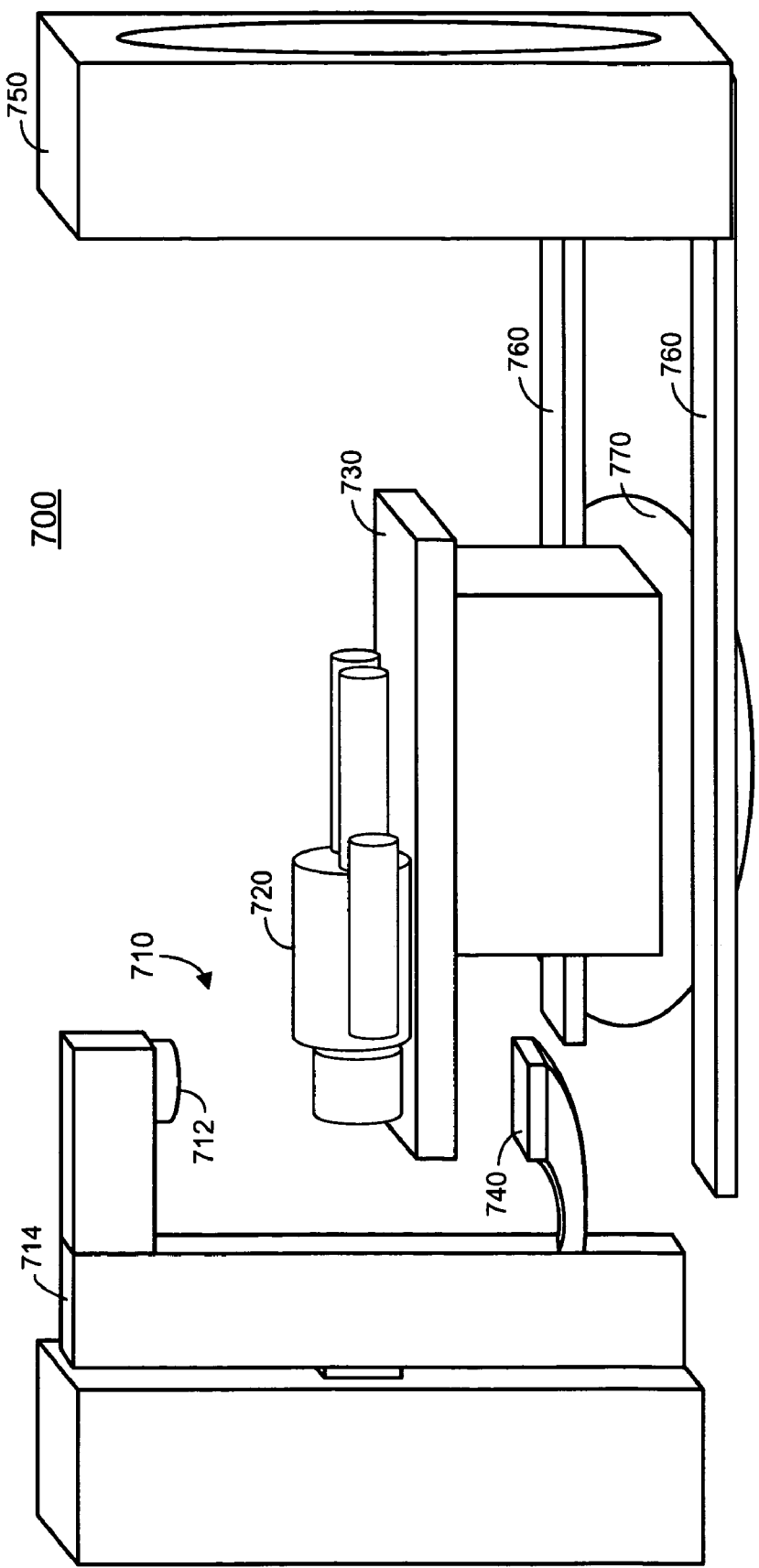
FIG. 12 is a perspective view of a radiation therapy system according to some embodiments.

FIG. 12 illustrates yet another system to acquire the three-dimensional image data at S501. System 700 includes linear accelerator 710 comprising treatment head 712 for emitting megavoltage treatment radiation toward patient 720 positioned on table 730. Gantry 714 may be rotated to allow emission of the radiation at various angles with respect to patient 730. Imaging device 740 may capture portal images of the emitted radiation.

According to system 700, three-dimensional image data is acquired at S501 by computed tomography (CT) scanner 750. CT scanner 750 includes an X-ray source and a radiation receiver that are mounted to face one another on opposite sides of a ring. Patient 230 may be positioned within the ring so that a portion of patient 230 lies between the X-ray source and the radiation receiver. The X-ray source then emits X-ray radiation that passes through the internal patient portion and is received by the radiation receiver as the ring rotates around the patient. A three-dimensional image of the patient portion may be generated from the radiation received by the radiation receiver using known reconstruction techniques.

Rails 760 and base 770 are used to position patient 230 within the ring as described above. Base 770 may initially rotates table 730 180 degrees from the position shown in FIG. 12. Next, CT scanner 750 moves along rails 760 toward table 730 until the portion of patient 230 is correctly positioned within the ring. After acquisition of the three-dimensional image, CT scanner 750 is moved away from table 730 and table 730 is rotated 180 degrees back to the position shown in FIG. 12. In some embodiments, system 700 comprises the PRIMATOM™ system sold by Siemens Medical Solutions.

Returning to process steps 500, a position offset is determined at S502 based on the three-dimensional data and on the first image data that was described with respect to process steps 100. Operator station 220 may determine the position offset by executing program code of rigid image registration module 335 to perform a three-dimensional rigid image-image registration based on the first image data and the acquired three-dimensional image data. In some embodiments, the first image data defines particular structures of patient 230, and the position offset is determined by perform a three-dimensional rigid structure-image registration based on the first image data and the acquired three-dimensional image data.

The patient may then be moved at S503 based on the determined position offset. Such movement may occur as described above with respect to step S404 of process steps 400.

Figure 13:
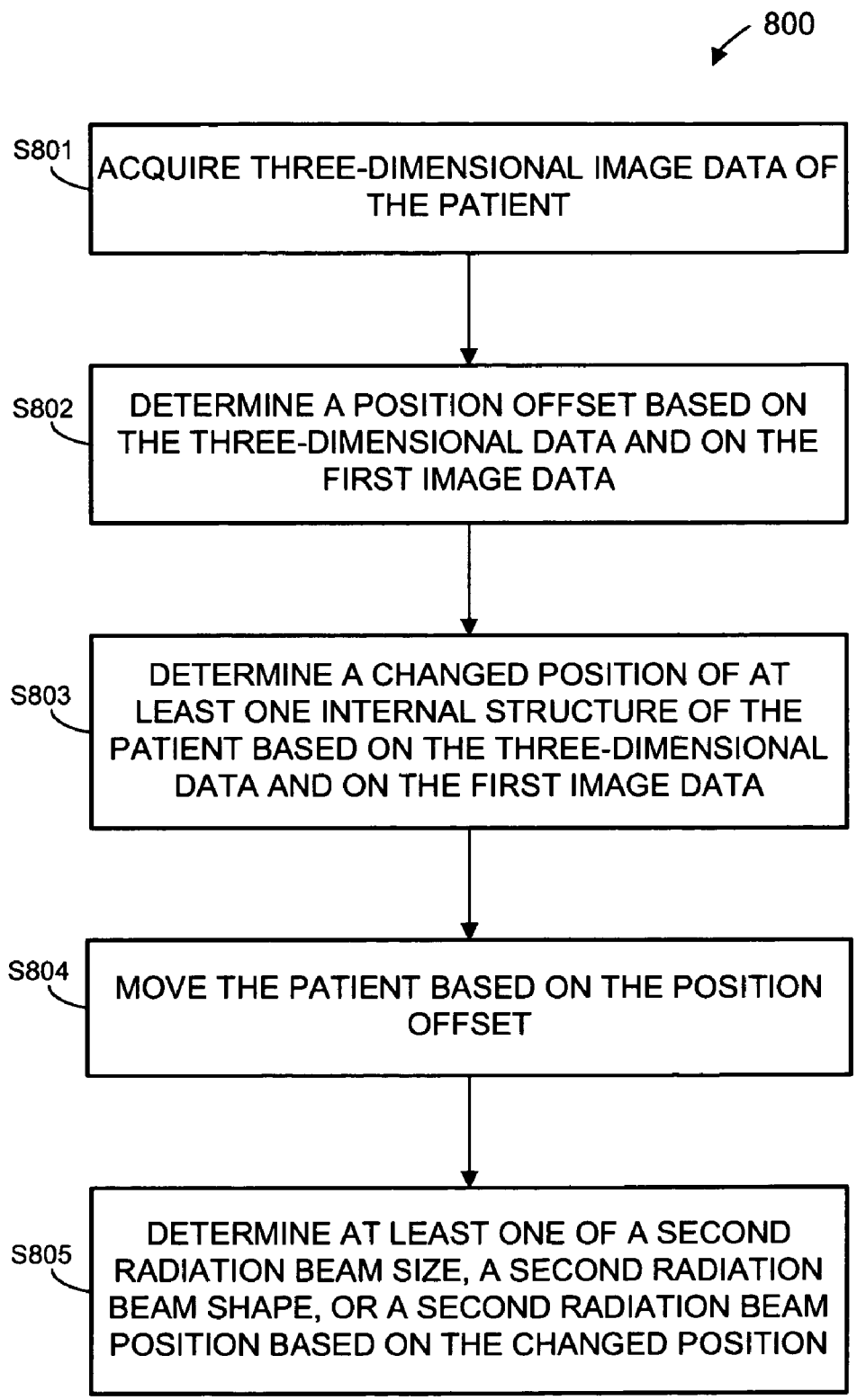
FIG. 13 comprises a flow diagram illustrating an adaptive radiation therapy process according to some embodiments.

FIG. 13 is a flow diagram of process steps 800 representing a SGRT process according to some embodiments. Three-dimensional image data of the patient is initially acquired at S801 using any of the systems and/or techniques mentioned above. Next, a position offset is determined at S802 based on the three-dimensional data and on the first image data that was described with respect to process steps 100. Operator station 220 may determine the position offset by executing program code of non-rigid image registration module 340 to perform a three-dimensional non-rigid image-image registration based on the first image data and the acquired three-dimensional image data.

A changed position of at least one internal structure of the patient is determined at S803. The changed position is determined based on the acquired three-dimensional data and on the first data. The first image data defines particular structures of patient 230, and the changed position is determined by performing a three-dimensional non-rigid structure-image registration based on the first image data and the acquired three-dimensional image data. Non-rigid image registration module 340 may also be employed for the determination of S803.

The patient may then be moved at S804 based on the determined position offset by moving table 250 as described above. Next, at S805, at least one new radiation beam parameter is determined based on the changed position. The at least one parameter may include a radiation beam size, a radiation beam position, and/or a radiation beam position. The new parameter(s) is intended to compensate for the changed position of the internal structure(s). In some embodiments of S805, operator station 220 executes program code of beam plan adjustment module to determine a change to at least one of the beam shape, beam size, or beam location determined at S101.

Figure 14:
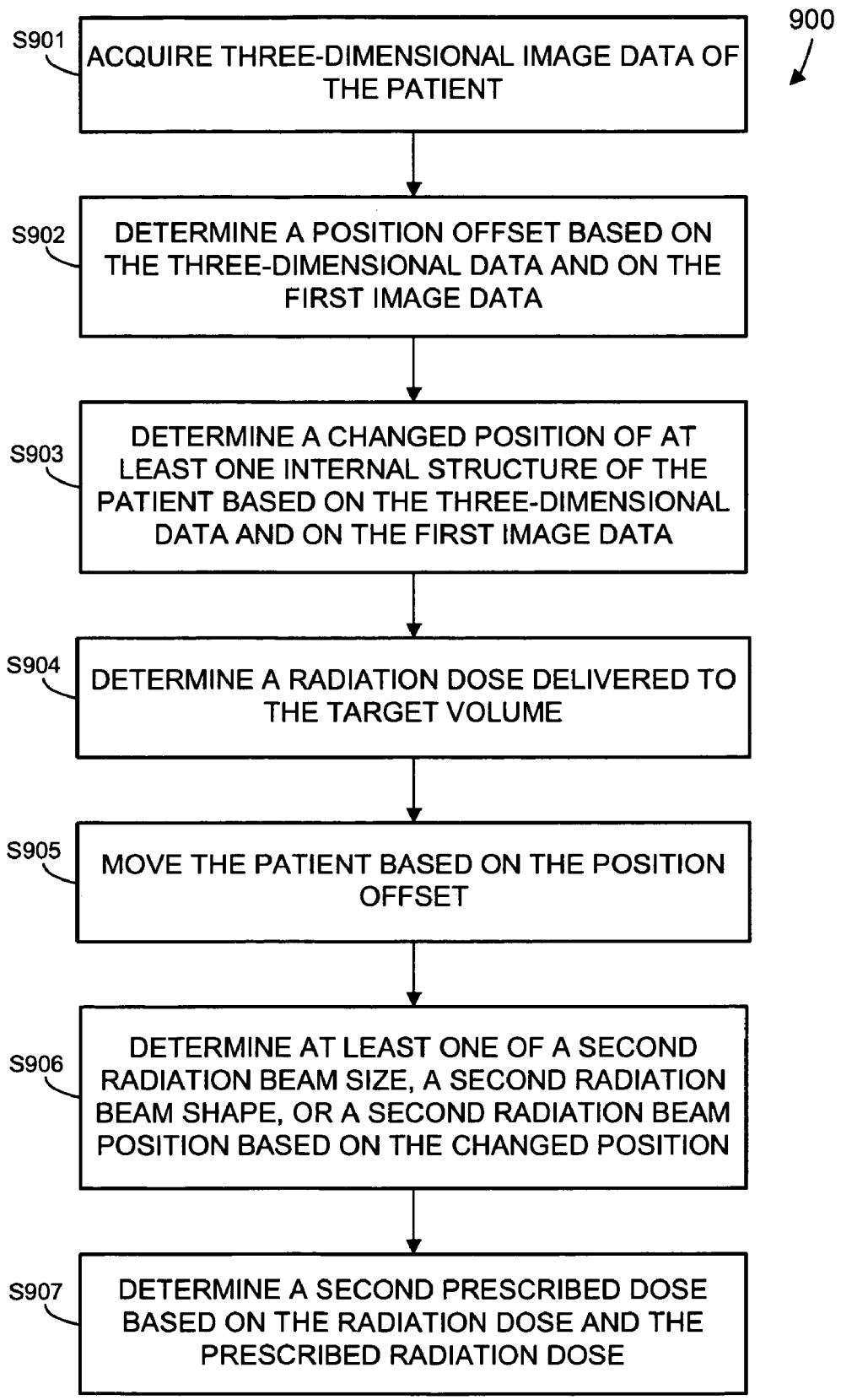
FIG. 14 comprises a flow diagram illustrating an adaptive radiation therapy process according to some embodiments.

FIG. 14 is a flow diagram of process steps 900 representing a DGRT process (step S106) according to some embodiments. Steps S901 through S903 may proceed as described above with respect to process steps S801 through S803. At S904, an actual radiation dose delivered to the target volume is determined. Of course, radiation must be delivered to the target volume sometime prior to S904.

During such delivery, an imaging device such as imaging device 240 may acquire exit dose information. Three-dimensional dose calculation module 350 may be utilized to determine the delivered radiation dose based on the exit dose information and using any algorithms that are or become known, including but not limited to Monte Carlo-type simulations.

The patient is moved at S905 based on the determined position offset by moving table 250 as described above. At least one new radiation beam parameter is then determined at S906 based on the changed position as described with respect to S805. The associated treatment plan may be retrieved from treatment plans 325, modified based on the new parameter(s), and re-stored therein. As mentioned above, the new parameter(s) is intended to compensate for the changed position determined at S903.

A second prescribed dose is determined at S907 based on the determined radiation dose and the prescribed dose mentioned with respect to step S101. According to some embodiments, operator station 220 executes program code of three-dimensional dose adjustment module 355 to determine the second prescribed dose. Module 355 may utilize module 340 to execute a three-dimensional dose-image registration based on the dose determined at S904 and on the first image data. Any other systems for determining the second prescribed dose may be employed at S907.

FIG. 15 is a tabular summary of a plurality of adaptive radiation therapy processes according to some embodiments. Table 1000 reflects aspects of the adaptive radiation therapy processes mentioned above. Embodiments are not limited to and do not necessarily include all of the above-mentioned processes.

Those in the art will appreciate that various adaptations and modifications of the above-described embodiments can be configured without departing from the scope and spirit of the claims. Therefore, it is to be understood that the claims may be practiced other than as specifically described herein.

What is claimed is:

1. A system comprising:
a microprocessor; and
a memory coupled to the microprocessor, the memory to store first image data of a patient and processor-executable program code, the program code executable by the microprocessor to select one radiation therapy process from an available first process and second process,
wherein the first radiation therapy process comprises acquisition of two-dimensional image data of the patient, determination of a position offset based on the two-dimensional image data and on the first image data, and movement of the patient based on the position offset, and
wherein the second radiation therapy process comprises acquisition of three-dimensional image data of the patient, determination of a second position offset based on the three-dimensional image data and on the first image data, and movement of the patient based on the second position offset.

2. A system according to claim 1, wherein selection of the one radiation therapy process comprises:
selection of the one radiation therapy process from the first radiation therapy process, the radiation therapy second process, and an available third radiation therapy process,
wherein the third radiation therapy process comprises:
acquisition of second three-dimensional image data of the patient;
determination of a third position offset based on the second three-dimensional image data and on the first image data;
determination of a changed position of at least one internal structure of the patient based on the second three-dimensional image data and on the first image data;
movement of the patient based on the third position offset; and
determination of at least one of a radiation beam size, a radiation beam shape, or a radiation beam position based on the changed position.

3. A system according to claim 2,
wherein determination of the position offset comprises rigid registration of the two-dimensional image data and a digitally-reconstructed radiograph based on the first image data,
wherein determination of the second position offset comprises rigid registration of the three-dimensional image data and on third three-dimensional image data based on the first image data,
wherein determination of the third position offset comprises non-rigid registration of the second three-dimensional image data and on fourth three-dimensional image data based on the first image data, and
wherein determination of the at least one of the radiation beam size, the radiation beam shape, or the radiation beam position comprises registration of a portion of the second three-dimensional image data representing the internal structure and the non-rigidly registered fourth three-dimensional image data.

4. A system according to claim 2, wherein selection of the one radiation therapy process comprises:
selection of the one radiation therapy process from the first radiation therapy process, the second radiation therapy process, the third radiation therapy process, and an available fourth radiation therapy process,
wherein the fourth radiation therapy process comprises:
acquisition of third three-dimensional image data of the patient;
determination of a fourth position offset based on the third three-dimensional image data and on the first image data;
determination of a second changed position of at least a second one internal structure of the patient based on the third three-dimensional image data and on the first image data;
determination of a radiation dose delivered to a target volume of the patient;
movement of the patient based on the fourth position offset;
determination of at least one of a second radiation beam size, a second radiation beam shape, or a second radiation beam position based on the second changed position; and
determination of a prescribed radiation dose based on the radiation dose and a previously-prescribed radiation dose for the target volume.

5. A system according to claim 4,
wherein determination of the position offset comprises rigid registration of the two-dimensional image data and a digitally-reconstructed radiograph based on the first image data,
wherein determination of the second position offset comprises rigid registration of the three-dimensional image data and on fourth three-dimensional image data based on the first image data,
wherein determination of the third position offset comprises non-rigid registration of the second three-dimensional image data and on fifth three-dimensional image data based on the first image data,
wherein determination of the at least one of the second radiation beam size, the second radiation beam shape, or the second radiation beam position comprises registration of a portion of the second three-dimensional image data representing the internal structure and the non-rigidly registered fifth three-dimensional image data,
wherein determination of the fourth position offset comprises non-rigid registration of the third three-dimensional image data and on sixth three-dimensional image data based on the first image data,
wherein determination of the at least one of the third radiation beam size, the third radiation beam shape, or the third radiation beam position comprises registration of a portion of the third three-dimensional image data representing the internal structure and the non-rigidly registered sixth three-dimensional image data, and
wherein determination of the second prescribed radiation dose comprises registration of seventh three-dimensional image data representing the previously-prescribed dose and the non-rigidly registered sixth three-dimensional image data.

6. A system according to claim 4, further comprising:
a radiation therapy delivery system to deliver radiation therapy according to the selected one radiation therapy process, wherein, after delivery of the radiation therapy, the program code is further executable by the microprocessor to select another one of the first radiation therapy process, the second radiation therapy process, the third radiation therapy process, and the fourth radiation therapy process.

7. A method comprising:

determining a radiation beam size, radiation beam shape, and radiation beam position for delivering at least a portion of a prescribed radiation dose to a target volume based on first image data of a patient; and selecting one radiation therapy process from an available first process and second process, wherein the first radiation therapy process comprises acquisition of two-dimensional image data of the patient, determination of a position offset based on the two-dimensional image data and on the first image data, and movement of the patient based on the position offset, and wherein the second radiation therapy process comprises acquisition of three-dimensional image data of the patient, determination of a second position offset based on the three-dimensional image data and on the first image data, and movement of the patient based on the second position offset.

8. A method according to claim 7, wherein selecting the one radiation therapy process comprises:

selecting the one radiation therapy process from the first radiation therapy process, the radiation therapy second process, and an available third radiation therapy process, wherein the third radiation therapy process comprises:

acquisition of second three-dimensional image data of the patient;

determination of a third position offset based on the second three-dimensional image data and on the first image data;

determination of a changed position of at least one internal structure of the patient based on the second three-dimensional image data and on the first image data;

movement of the patient based on the third position offset; and determination of at least one of a second radiation beam size, a second radiation beam shape, or a second radiation beam position based on the changed position.

9. A method according to claim 8, wherein determination of the position offset comprises rigid registration of the two-dimensional image data and a digitally-reconstructed radiograph based on the first image data, wherein determination of the second position offset comprises rigid registration of the three-dimensional image data and on third three-dimensional image data based on the first image data, wherein determination of the third position offset comprises non-rigid registration of the second three-dimensional image data and on fourth three-dimensional image data based on the first image data, and wherein determination of the at least one of the second radiation beam size, the second radiation beam shape, or the second radiation beam position comprises registration of a portion of the second three-dimensional image data representing the internal structure and the non-rigidly registered fourth three-dimensional image data.

10. A method according to claim 8, wherein selecting the one radiation therapy process comprises:

selecting the one radiation therapy process from the first radiation therapy process, the second radiation therapy process, the third radiation therapy process, and an available fourth radiation therapy process, wherein the fourth radiation therapy process comprises:

acquisition of third three-dimensional image data of the patient;

determination of a fourth position offset based on the third three-dimensional image data and on the first image data;

determination of a second changed position of at least a second one internal structure of the patient based on the third three-dimensional image data and on the first image data;

determination of a radiation dose delivered to the target volume;

movement of the patient based on the fourth position offset;

determination of at least one of a third radiation beam size, a third radiation beam shape, or a third radiation beam position based on the second changed position; and determination of a second prescribed radiation dose based on the radiation dose and the prescribed radiation dose.

11. A method according to claim 10, wherein determination of the position offset comprises rigid registration of the two-dimensional image data and a digitally-reconstructed radiograph based on the first image data, wherein determination of the second position offset comprises rigid registration of the three-dimensional image data and on fourth three-dimensional image data based on the first image data, wherein determination of the third position offset comprises non-rigid registration of the second three-dimensional image data and on fifth three-dimensional image data based on the first image data, wherein determination of the at least one of the second radiation beam size, the second radiation beam shape, or the second radiation beam position comprises registration of a portion of the second three-dimensional image data representing the internal structure and the non-rigidly registered fifth three-dimensional image data, wherein determination of the fourth position offset comprises non-rigid registration of the third three-dimensional image data and on sixth three-dimensional image data based on the first image data, wherein determination of the at least one of the third radiation beam size, the third radiation beam shape, or the third radiation beam position comprises registration of a portion of the third three-dimensional image data representing the internal structure and the non-rigidly registered sixth three-dimensional image data, and wherein determination of the second prescribed radiation dose comprises registration of seventh three-dimensional image data representing the prescribed dose and the non-rigidly registered sixth three-dimensional image data.

12. A method according to claim 10, further comprising:

delivering radiation therapy according to the selected one radiation therapy process; and selecting another one of the first radiation therapy process, the second radiation therapy process, the third radiation therapy process, and the fourth radiation therapy process.

13. A medium storing processor-executable program code, the program code comprising:
   code to determine a radiation beam size, radiation beam shape, and radiation beam position for delivering at least a portion of a prescribed radiation dose to a target volume based on first image data of a patient; and
   code to select one radiation therapy process from an available first process and second process,
   wherein the first radiation therapy process comprises acquisition of two dimensional image data of the patient, determination of a position offset based on the two-dimensional image data and on the first image data, and movement of the patient based on the position offset, and
   wherein the second radiation therapy process comprises acquisition of three-dimensional image data of the patient, determination of a second position offset based on the three-dimensional image data and on the first image data, and movement of the patient based on the second position offset.

14. A medium according to claim 13, wherein the code to select the one radiation therapy process comprises:
   code to select the one radiation therapy process from the first radiation therapy process, the radiation therapy second process, and an available third radiation therapy process,
   wherein the third radiation therapy process comprises:
      acquisition of second three-dimensional image data of the patient;
      determination of a third position offset based on the second three-dimensional image data and on the first image data;
      determination of a changed position of at least one internal structure of the patient based on the second three-dimensional image data and on the first image data;
      movement of the patient based on the third position offset; and
      determination of at least one of a second radiation beam size, a second radiation beam shape, or a second radiation beam position based on the changed position.

15. A medium according to claim 14,
   wherein determination of the position offset comprises rigid registration of the two-dimensional image data and a digitally-reconstructed radiograph based on the first image data,
   wherein determination of the second position offset comprises rigid registration of the three-dimensional image data and on third three-dimensional image data based on the first image data,
   wherein determination of the third position offset comprises non-rigid registration of the second three-dimensional image data and on fourth three-dimensional image data based on the first image data, and
   wherein determination of the at least one of the second radiation beam size, the second radiation beam shape, or the second radiation beam position comprises registration of a portion of the second three-dimensional image data representing the internal structure and the non-rigidly registered fourth three-dimensional image data.

16. A medium according to claim 14, wherein the code to select the one radiation therapy process comprises:
   code to select the one radiation therapy process from the first radiation therapy process, the second radiation therapy process, the third radiation therapy process, and an available fourth radiation therapy process,
   wherein the fourth radiation therapy process comprises:
      acquisition of third three-dimensional image data of the patient;
      determination of a fourth position offset based on the third three-dimensional image data and on the first image data;
      determination of a second changed position of at least a second one internal structure of the patient based on the third three-dimensional image data and on the first image data;
      determination of a radiation dose delivered to the target volume;
      movement of the patient based on the fourth position offset;
      determination of at least one of a third radiation beam size, a third radiation beam shape, or a third radiation beam position based on the second changed position; and
      determination of a second prescribed radiation dose based on the radiation dose and the prescribed radiation dose.

17. A medium according to claim 16,
   wherein determination of the position offset comprises rigid registration of the two-dimensional image data and a digitally-reconstructed radiograph based on the first image data,
   wherein determination of the second position offset comprises rigid registration of the three-dimensional image data and on fourth three-dimensional image data based on the first image data,
   wherein determination of the third position offset comprises non-rigid registration of the second three-dimensional image data and on fifth three-dimensional image data based on the first image data,
   wherein determination of the at least one of the second radiation beam size, the second radiation beam shape, or the second radiation beam position comprises registration of a portion of the second three-dimensional image data representing the internal structure and the non-rigidly registered fifth three-dimensional image data,
   wherein determination of the fourth position offset comprises non-rigid registration of the third three-dimensional image data and on sixth three-dimensional image data based on the first image data,
   wherein determination of the at least one of the third radiation beam size, the third radiation beam shape, or the third radiation beam position comprises registration of a portion of the third three-dimensional image data representing the internal structure and the non-rigidly registered sixth three-dimensional image data, and
   wherein determination of the second prescribed radiation dose comprises registration of seventh three-dimensional image data representing the prescribed dose and the non-rigidly registered sixth three-dimensional image data.

18. A medium according to claim 16, the code further comprising:
   code to control a radiation therapy device to deliver radiation therapy according to the selected one radiation therapy process; and
   code to select another one of the first radiation therapy process, the second radiation therapy process, the third radiation therapy process, and the fourth radiation therapy process.

* * * * *